United States Patent [19]
Corfitsen et al.

[11] Patent Number: 5,364,353
[45] Date of Patent: Nov. 15, 1994

[54] APPARATUS FOR ADVANCING AN OBJECT THROUGH A BODY PASSAGE

[76] Inventors: Mogens T. Corfitsen, Skodsborg Strandvej 220A, DK-2942 Skodsborg; Henrik Harboe, Tollosevej 39, DK-2700 Bronshoj; Erik Othel-Jacobsen, Turbinevej 7, DK-3150 Hellebaek, all of Denmark

[21] Appl. No.: 104,044
[22] PCT Filed: Feb. 24, 1992
[86] PCT No.: PCT/DK92/00054
 § 371 Date: Nov. 24, 1993
 § 102(e) Date: Nov. 24, 1993
[87] PCT Pub. No.: WO92/14507
 PCT Pub. Date: Sep. 3, 1992

[30] Foreign Application Priority Data
Feb. 25, 1991 [DK] Denmark ................. 320/91

[51] Int. Cl.⁵ .................... A61M 37/00; A61B 1/00
[52] U.S. Cl. .................... 604/95; 604/96; 128/4
[58] Field of Search ............. 128/4, 6, 7-10; 604/95, 96; 73/866.5, 865.8

[56] References Cited
U.S. PATENT DOCUMENTS

| | | |
|---|---|---|
| 3,895,637 | 7/1975 | Choy . |
| 4,176,662 | 12/1979 | Frazer . |
| 4,195,529 | 4/1980 | Madoian et al. . |
| 4,372,161 | 2/1983 | de Buda et al. . |
| 4,690,131 | 9/1987 | Lyddy, Jr. et al. ............. 128/4 |
| 5,144,848 | 9/1992 | Uenishi et al. ............. 128/4 X |

FOREIGN PATENT DOCUMENTS

| | | | |
|---|---|---|---|
| 366904 | 5/1982 | Austria . | |
| 1549420 | 10/1967 | France . | |
| 2827473C2 | 1/1979 | Germany . | |
| 3425483C2 | 1/1986 | Germany . | |
| 1216238 | 8/1989 | Japan ............. | 128/4 |
| 1216239 | 8/1989 | Japan ............. | 128/4 |
| 1216240 | 8/1989 | Japan ............. | 128/4 |
| 1604380 | 11/1990 | Switzerland ......... | 604/96 |

Primary Examiner—Richard J. Apley
Assistant Examiner—John P. Leubecker
Attorney, Agent, or Firm—Finnegan, Henderson, Farabow, Garrett & Dunner

[57] ABSTRACT

An intestinal probe comprises a bladder and an axially expandable bellows connected with the bladder and being designed such that it changes its dimensions reversibly in its axial direction dependent on the pressure in its interior. A tube is provided with a lumen for the supply and removal of inflation medium to the bladder and bellows, the bladder and bellows being interconnected through a throttling valve. The throttling valve ensures that the inflation of the bladder is delayed relative to the axial expansion of the bellows and that the deflation of the bladder is delayed relative to an axial contraction of the bellows so that the intestinal probe, by using one lumen only for inflation medium, can be advanced stepwise through a gastrointestinal canal.

7 Claims, 3 Drawing Sheets

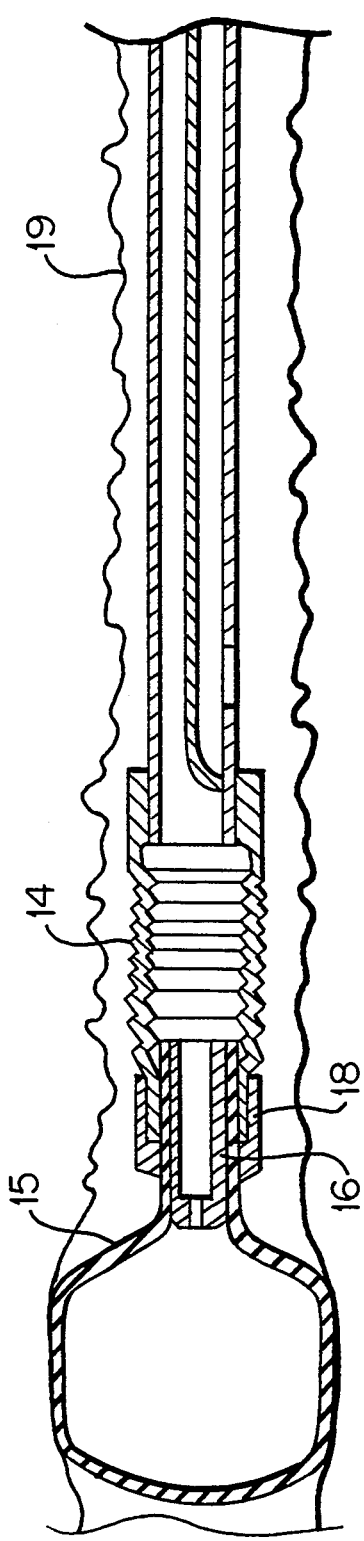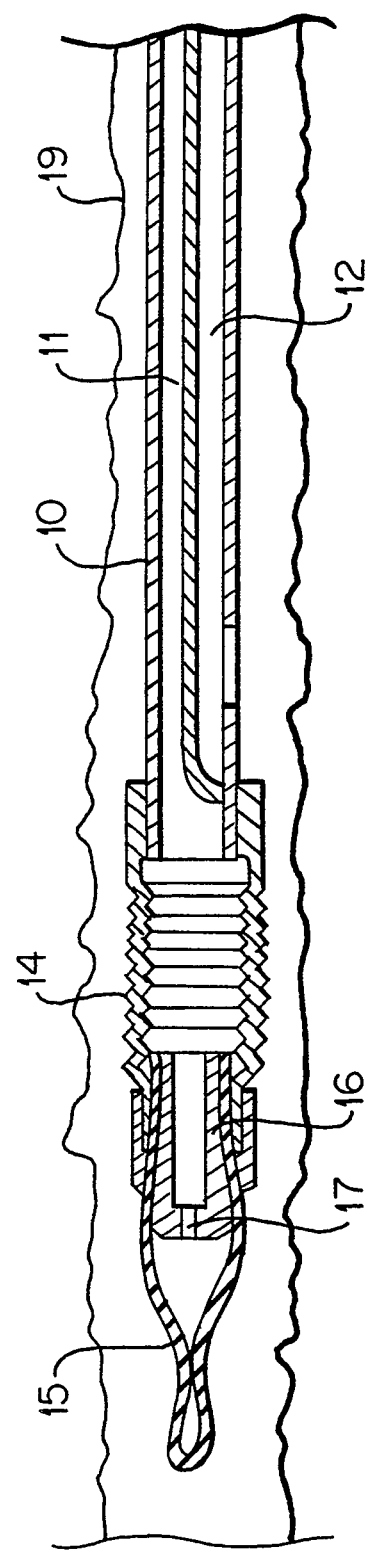
FIG. 5
FIG. 6

APPARATUS FOR ADVANCING AN OBJECT THROUGH A BODY PASSAGE

BACKGROUND OF THE INVENTION

The present invention relates to an apparatus for advancing an object through a body passage comprising a radially expandable hollow member and an axially expandable hollow member connected to said radially expandable hollow member, said axially expandable hollow member designed such that it changes dimensions reversibly in its axial direction dependent on the pressure in the interior of the axially expandable hollow member, and a tube with a lumen for the supply and removal of inflation medium to the axially expandable hollow member.

The invention relates in particular to an intestinal probe for use in the evacuation of the intestinal waste from the gastro-intestinal canal.

Intestinal probes are useful e.g. in the treatment of early postoperative adhesion ileus (adhesions in the abdominal cavity), repeated late postoperative adhesion ileus, carcinomatosis peritonei (cancerous growth in the abdominal cavity), intestinal hematoma (hemorrhage in the abdominal cavity) in patients under anti-coagulation treatment and in the treatment of technically inoperable patients.

Prior art intestinal probes consist of a bladder mounted at the distal end of an aspiration tube provided with an additional lumen for the supply of inflation medium to the interior of the bladder.

In the treatment of the kind of disorders described above using the known intestinal probes, the probe is advanced through the nostril to the ventricle and out through the pylorus. The bladder is subsequently partially inflated with air and mercury, whereupon the gastric peristalsis in a gastrically healthy patient gradually and over a period of several hours, e.g. 6–10 hours, carries the intestinal probe all the way through the enteric system to the ileus site. In an ileus patient the intestinal probe advances considerably slower, because the intestinal functions is compromised by oedema in the intestinal lumen and the resulting fluid and electrolyte disturbances. In such cases it may take days before the bladder reaches the ileus-inflicted Intestinal regions.

When the bladder is positioned in an ileus-inflicted Intestinal region, a subatmospheric pressure is established in the aspiration conduit and the intestinal waste is evacuated from the intestine thereby establishing a normal intestinal peristalsis thus allowing the bladder to be carried on to other ileus-inflicted regions.

Whether a normal intestinal function can be reestablished with known intestinal probes depends on the etiology of the acute ileus condition.

In a number of cases the intestinal functioning of the distal end of an ileus-inflicted region is compromised to such an extent that evacuation of the intestines in the proximal area is not sufficient for the reestablishment of normal intestinal functions. In such cases the intestine is not capable of further advancing the intestinal probe and the desired effect of the treatment cannot be achieved.

In the known intestinal probes the bladder serves to impart to the front part of the probe a diameter which is sufficient for the intestinal peristalsis to influence the intestinal probe and thereby advance it through the intestinal canal.

U.S. Pat. No. 4,176,662 discloses an endoscope having a propulsion mechanism consisting of two bladders and an axially expandable bellows separating said two bladders, and three different air tubes for selectively conducting inflation air to the bladders and the bellows. The propulsion mechanism is operated by initially supplying air to the proximal bladder while the bellows and the distal bladder are in their deflated condition. The supply is continued until the outside of the proximal bladder abuts the intestinal wall and thus secures the endoscope relative to the intestine. Air is subsequently supplied to the bellows thereby expanding it axially and provoking a propulsion of the front end of the endoscope. The distal bladder is then brought to expand until its outside abuts the intestinal wall and the front part of the endoscope is immobilized. A subsequent deflation of the proximal bladder and sequentially of the bellows, causes the bellows to contract and to pull the deflated proximal bladder and the tube onwards in the intestine. Following a final deflation of the distal bladder the cycle may be repeated.

As it appears from the above the functioning of the known propulsion mechanism is conditioned by the presence of three different air tubes and by careful control of the supply and evacuation of air through the tubes.

SUMMARY OF THE INVENTION

The apparatus according to the present invention which apparatus is characterized in that the axially expandable hollow member and the radially expandable member are interconnected through a throttling means, presents the important advantage that it is simpler in construction as well as handling than the known propulsion mechanism as will appear from the following description of its functioning.

Following the insertion into the body passage, e.g. the gastro-intestinal canal, of the part of the apparatus comprising the radially expandable bladder (in the following referred to as the bladder) and the axially expandable hollow member an inflation medium is supplied under pressure to the axially expandable hollow member. Thereby the length of the hollow member is increased. Due to the bendings of the apparatus tube there will be considerable resistance to the apparatus tube being pushed rearwards once the apparatus has been inserted into the gastro-intestinal canal. Consequently an increase of the length of the axially expandable hollow member will result in an advancement of the bladder in the gastro-intestinal canal. When the throttling means is suitably designed the flow of inflation medium from the axially expandable hollow member to the bladder will be delayed sufficiently to ensure that the bladder will only be in a minimally inflated condition when the axially expandable member has reached the maximum length corresponding to the superatmospheric pressure used. Subsequently, however, identical pressures will be established in the bladder and in the axially expandable hollow member, and thus the bladder will expand to such an extent that it provokes an inflation of the intestinal wall. Thereby the bladder is immobilized relative to the intestine.

The pressure in the axially expandable hollow member is then caused to decrease. This may happen by means of a simple pressure relief or by evacuation of inflation medium.

The throttling means causes the decrease of pressure to occur at a slower rate in the bladder which consequently remains expanded whereas the axially expandable hollow member contracts and pulls the tube some distance onwards through the gastro-intestinal canal.

When the pressure has later been equalized in the bladder, the latter as well as the axially expandable hollow member are in such a condition that a renewed cycle and hence a further advancement step for the tube may be implemented.

In this way the tube is rapidly carried to the ileus-inflicted region and once arrived an aspiration of intestinal waste may be implemented on this site and, if desired, so may an inflation of the intestinal wall in order to overcome obstructions, if any, The use of a simplified test apparatus has proved it possible to advance an aspiration tube through the gastro-intestinal canal at a travelling rate of 9 cm/min and it is expected that such travelling rate may be increased to more than 25 cm/min with the result that an intestinal probe may be carried to the ileus site in less than an hour.

While it is desirable that the hollow member is capable of expanding drastically in its axial direction, its radial expansion should be small or at least not so extensive that the pressures applied provoke an inacceptable inflation of the intestine.

According to the invention the axially expandable hollow member preferably consists of a rubber or plastics bellows.

Preferably the radially expandable hollow member consists of a rubber or plastics bladder.

A cylindrical connecting means of e.g. plastics is preferably mounted between the distal end of the axially expandable hollow member and the proximal end of the bladder.

The throttling means may be a throttling valve of a known type. According to the invention, a particularly simple and reliable throttling means consists of a narrow passage provided in the above connecting means between the bladder and the hollow member.

Examples of inflation media are gaseous media, such as air, and/or liquid media, such as water.

The invention will now be described in further detail with reference to the accompanying drawing, wherein

BRIEF DESCRIPTION OF THE DRAWINGS

FIG. 1 is a schematical view of an intestinal probe according to the invention which has been inserted into a human gastro-intestinal canal and FIGS. 2-6 are longitudinal views of the front end of an intestinal probe according to the invention inserted into a gastro-intestinal canal and showing different stages of an advancing cycle.

DESCRIPTION OF THE PREFERRED EMBODIMENTS

Figure 1:
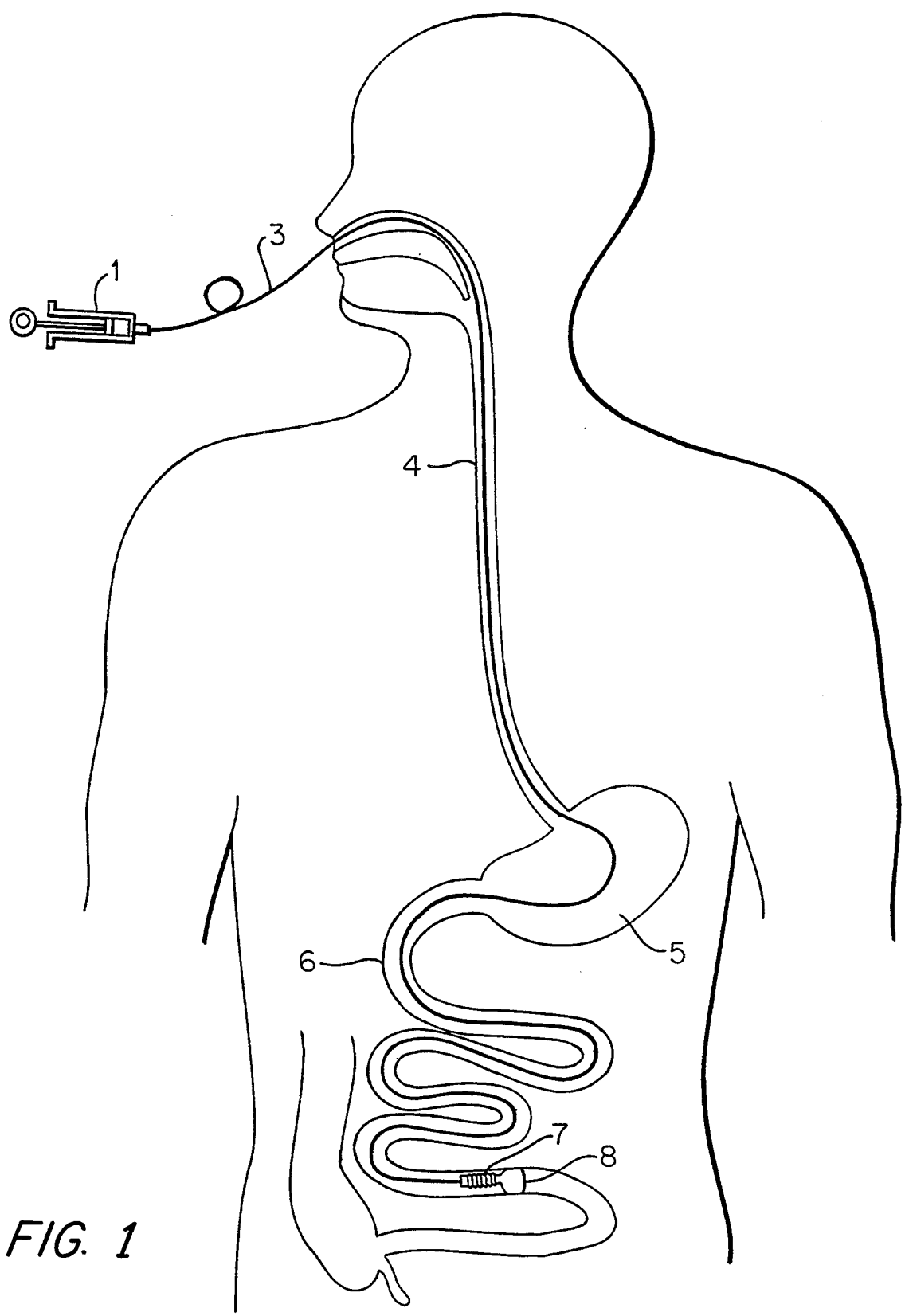

In FIG. 1, 1 denotes a piston pump connected to an intestinal probe comprising a tube 3 extending through the gullet 4 of a human being, his stomach 5 and small intestine 6, 7 a bellows and 8 a bladder.

The intestinal probe shown in FIGS. 2-6 comprises a double-lumen tube 10 comprising a lumen 11 for inflation air and an aspiration lumen 12 provided with an orifice 13 in the conduit wall.

The distal end of the tube 10 is connected to the proximal end of a bellows 14, the lumen 11 being in communication with the interior of the bellows 14.

The intestinal probe shown further comprises an inflatable bladder 15 and a connector 16 having an internal narrow conduit 17 between the bellows 14 and the bladder 15, the distal end of the bellows 14 and the proximal end of the bladder 15 being squeezed together between the connector 16 and an annular shrink ring 18.

The intestinal probe shown is inserted into an intestinal canal 19.

Figure 2:
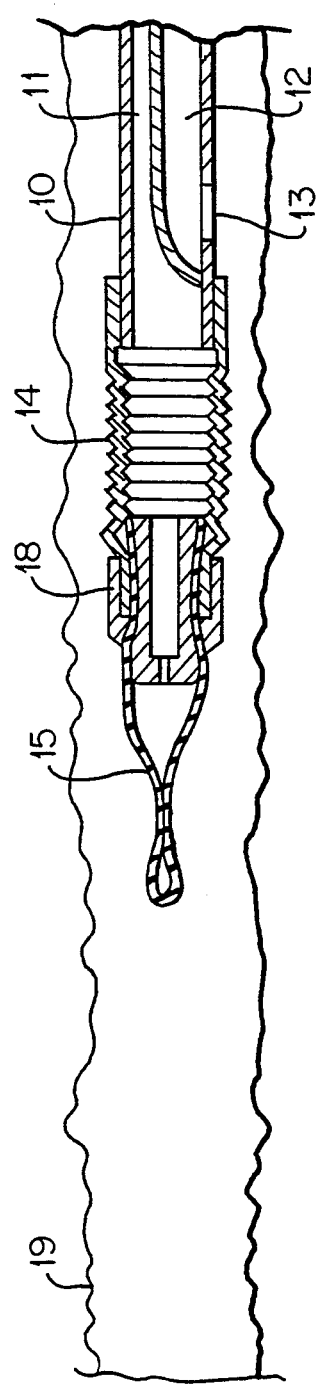

FIG. 2 shows the intestinal probe in its starting position, i.e. in a position where normal pressure is prevailing both in the bellows 14 and the bladder 15.

Figure 3:
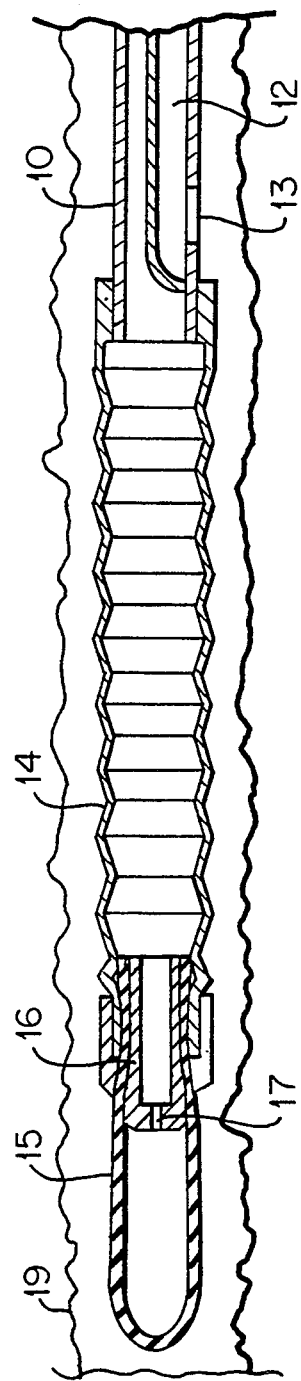

In the position shown in FIG. 3 a superatmospheric pressure is established in the bellows 14 but only a partial expansion of the bladder 15 has been generated because the air flow between the bellows 14 and the bladder 15 is restricted by the narrow conduit 17. The superatmospheric pressure in the bellows 14 has caused it to expand in its axial direction thereby causing the connector 16 and the bladder 15 to be moved some distance to the left.

Figure 4:
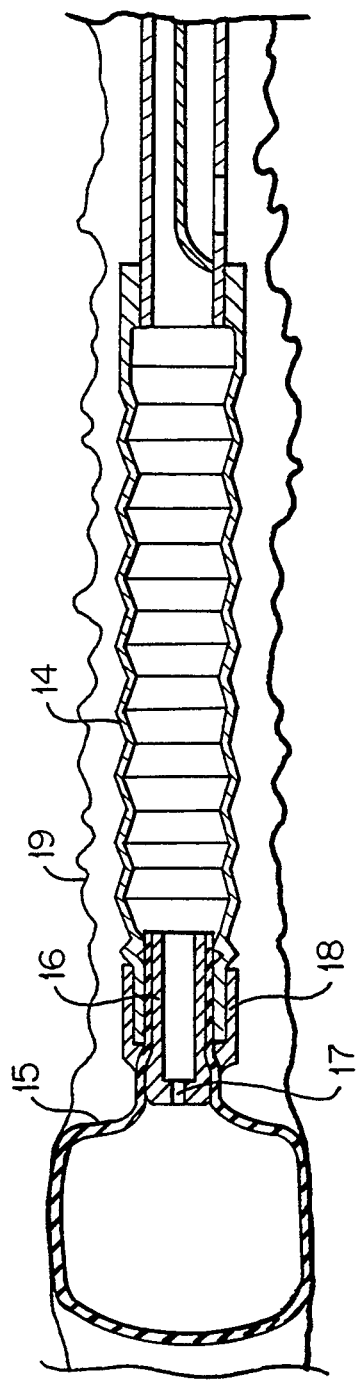

In the position shown in FIG. 4 a pressure equalization between the bellows 14 and the bladder 15 has taken place and the latter has thus become inflated to such an extent that it closely abuts the inside of the intestinal canal 19.

In the position shown in FIG. 5 the pressure in the bellows 14 has been reduced but no corresponding pressure reduction has yet occurred in the bladder 15. The pressure reduction in the bellows 14 has caused it to contract, and as the bladder 15 is still immobilized relative to the intestinal wall 19 also the tube 10 has been carried a step onwards to the left.

FIG. 6 shows the position of the intestinal probe following a pressure reduction in the bladder 15 and thus the starting position for a new cycle.

What is claimed is:

1. An apparatus for advancing an object through a body passage comprising:
   an axially expandable hollow member having a proximal end and a distal end, wherein said axially expandable hollow member is capable of changing dimensions reversibly in its axial direction dependent on the pressure in its interior;
   a radially expandable hollow member having a proximal end which is connected to said distal end of said axially expandable hollow member;
   a tube connected to said proximal end of said axially expandable hollow member, said tube having a lumen for the supply and removal of inflation medium to said axially expandable hollow member; and
   throttling means interconnecting said axially expandable hollow member and said radially expandable hollow member for restricting flow of inflation medium between each of said members, whereby pressure equalization between said members is delayed.

2. An apparatus according to claim 1, wherein the axially expandable hollow member consists of a rubber or plastic bellows.

3. An apparatus according to claims 1 or 2, wherein the radially expandable hollow member consists of a rubber or plastic bladder.

4. An apparatus according to claims 1 or 2, further including a cylindrical connecting means for connecting said distal end of said axially expandable hollow member and said proximal end of the radially expandable hollow member.

5. An apparatus according to claim 4, wherein the throttling means comprises a narrow conduit within said connecting means.

6. An apparatus according to claim 3, further including cylindrical connecting means for connecting said distal end of said axially expandable hollow member and said proximal end of the radially expandable hollow member.

7. An apparatus according to claim 6, wherein said throttling means comprises a narrow conduit within said connecting means.

* * * * *